United States Patent [19]

Philippe et al.

[11] Patent Number: 4,857,525
[45] Date of Patent: Aug. 15, 1989

[54] QUATERNARY AMMONIUM RETINOATES, THEIR USE IN COSMETICS AND IN DERMOPHARMACY

[75] Inventors: Michel Philippe, Drancy; Henri Sebag; Didier S. Leger, both of Paris; Jean L. Leveque, Montfermeil, all of France

[73] Assignee: L'Oreal, Paris, France

[21] Appl. No.: 190,441

[22] Filed: May 5, 1988

[30] Foreign Application Priority Data

May 6, 1987 [LU] Luxembourg ............... 86865

[51] Int. Cl.⁴ ............... A61K 31/205; A61K 31/535; C07D 295/14
[52] U.S. Cl. ............... 514/227.5; 514/231.2; 514/255; 514/317; 514/408; 514/554; 544/108; 544/58.1; 544/403; 546/192; 548/579; 562/510
[58] Field of Search ............... 260/501.15; 544/108, 544/58.1, 403; 546/192; 548/579; 562/510; 514/554, 231.2, 227.5, 255, 317, 408

[56] References Cited

U.S. PATENT DOCUMENTS 2,429,171 10/1947 Ruzicka et al. ............... 260/344.6
4,214,000 7/1980 Papa ............... 514/494

FOREIGN PATENT DOCUMENTS 1297730 5/1962 France .

Primary Examiner—Mary C. Lee
Assistant Examiner—MarySue Howard
Attorney, Agent, or Firm—Fleit, Jacobson, Cohn, Price, Holman & Stern

[57] ABSTRACT

Quaternary ammonium retinoate, characterized in that it corresponds to the formula:

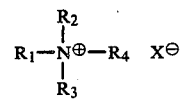

in which:
X— denotes either an all-trans-retinoate of formula (I):

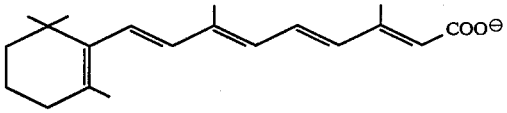

or a 13-cis retinoate of formula:

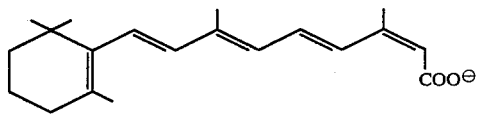

(i) $R_1$, $R_2$ and $R_3$, which may be identical or different, denote a saturated $C_1$–$C_4$ linear alkyl group capable of bearing one or more hydroxyl group(s) at the end of the chain or in the chain;
$R_4$ denotes a $C_{12}$–$C_{18}$ linear alkenyl or alkyl group;
(ii) $R_3$ denotes a group:

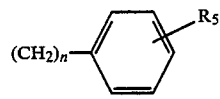

in which n equals 0 or 1, $R_5$ denotes a hydrogen atom, a hydroxyl, a halogen atom, a $C_1$–$C_{18}$-hydroxyl alkyl or alkyl group or a $C_2$ to $C_{18}$ acyl group;
$R_1$, $R_2$ and $R_4$ having the same meanings as those under (i);
(iii) $R_1$ and $R_2$ can form an aliphatic heterocycle optionally containing an oxygen atom, another nitrogen atom or a sulphur atom;
$R_3$ and $R_4$ having the same meanings as those under (i) and (ii).

8 Claims, No Drawings

QUATERNARY AMMONIUM RETINOATES, THEIR USE IN COSMETICS AND IN DERMOPHARMACY

The present invention relates to new quaternary ammonium derivatives, and more specifically to new quaternary ammonium retinoates, a process for preparing them and cosmetic and pharmaceutical compositions containing them.

In the prior art, a description has already been given of the use of different hexadecyltrimethyl ammonium salts, including the oleate, as a germicidal agent. [See, in particular, Gautier et al., Bull Soc. Chim. France (1955) (634)].

The Applicant has just discovered, and this forms the subject of the present invention, new quaternary ammonium retinoates. He has found that these new quaternary ammonium retinoates possessed an antibacterial activity with respect to strains of *Propionibacterium acnes*, and that these compounds could be used advantageously as antiseptic, comedolytic, keratolytic and wart-removing agents and/or as agents against various skin infections and in particular against infectious or non-infectious dermatoses which may be of bacterial or mycobacterial origin and/or linked to the implantation of certain yeasts having a pathogenic nature. They can also be used as anti-dandruff agents, or alternatively for stimulating hair regrowth and retarding hair loss.

The compounds according to the invention have also proved to have properties of counteracting ageing of the skin, in particular with respect to ageing due to solar radiation.

The Applicant has observed, in particular, that these compounds are especially effective in the treatment of acne.

As is well known, acne is a polymorphic skin disorder, occurring at puberty and regressing spontaneously, in most cases, at about 20 to 25 years of age. In effected individuals, acne effects all the areas that are rich in sebaceous glands (forehead, face, wings of the nose, trunk, back) with the exception of the scalp.

The acetiopathogenesis of acne, although poorly defined, owes it origin to the formation of a characteristic lesion, the comedo. The latter results from the obstruction of the pilosebaceous duct as a consequence of dyskeratinization of the region of the infundibulum of the duct.

This obstruction has the major effect of modifying the rheological properties of the sebum and the physico-chemical properties of the medium, such as pH, oxygen tension, and the like.

This modification permits the hyperproliferation of the cutaneous resident strains, mainly *Propionibacterium acnes*, which is an anaerobic or air-tolerant strain.

The bacterial hyperproliferation results in the release into the medium of certain proteases of hyaluronidases of bacterial origin, which cause lysis of the follicular sac and thereby the release of inflammatory compounds within the dermis and trigger the body's inflammatory type reaction.

While the nature of the inflammatory compounds is undetermined at the present time, their bacterial origin appears to be in little doubt, explaining the good therapeutic success in inflammatory acne of antibacterial compounds, administered either orally or topically.

With this object, antibacterial agents, for example antibiotics such as erythromycin, tetracycline and clindamycin, have very often been recommended in the treatment of acne. These compounds give excellent results, but their excessive use renders the strains of *Propionibacterium acnes* resistant to these same antibiotics, so that repeated treatment proves to have little effect.

The Applicant has discovered that the new quaternary ammonium retinoates possess an "in vitro" antibacterial activity with respect to *Propionibacterium acnes* close to that of the antibiotics used topically against acne, such as, in particular, erythromycin and clindamycin, without possessing the limitations of the latter compounds resulting from repeated use.

The Applicant has also found that the new quaternary ammonium retinoates have a comedolytic and keratolytic activity superior to that of hexadecyltrimethylammonium oleate.

The subject of the invention is hence, by way of new compounds, quaternary ammonium retinoates defined below.

Another subject of the invention consists of compositions containing the compounds defined above and which are usable in therapeutic treatments.

The subject of the invention is also a composition and a process for cosmetic treatment based on these compounds.

Other subjects of the invention will become apparent on reading the description and the examples which follow.

The quaternary ammonium retinoates which form the main subject of the invention are compounds corresponding essentially to the following formula (I):

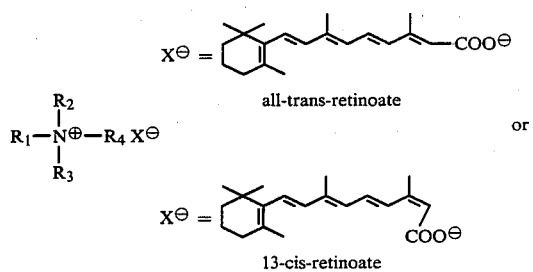

$$R_1-\overset{R_2}{\underset{R_3}{N^{\oplus}}}-R_4 \; X^{\ominus}$$

in which:
(i) $R_1$, $R_2$ and $R_3$, which may be identical or different, denote a saturated $C_1-C_4$ linear alkyl group capable of bearing one or more hydroxyl groups at the end of the chain or in the chain; $R_4$ denotes a $C_{12}-C_{18}$ linear alkenyl or alkyl group;
(ii) $R_3$ denotes a group;

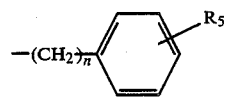

in which n equals 0 or 1, $R_5$ denotes a hydrogen atom, a hydroxyl, a halogen atom, a $C_1$ to $C_{18}$ hydroxyalkyl or alkyl group or a $C_2$ to C-18 acyl group, $R_1$, $R_2$ and $R_4$ having the meanings given above;
(iii) $R_1$ and $R_2$ can form an aliphatic heterocycle optionally containing an oxygen atom, another nitrogen atom or a sulphur atom, $R_3$ and $R_4$ having the meanings defined above in (i) and (ii).

The compounds according to the invention are preferably prepared from a salt such as, more especially, the corresponding quaternary ammonium carbonates solubilized in a solvent such as methanol, ethanol, isopropanol, tetrahydrofuran, dioxane or a mixture thereof, to which the chosen retinoic acid, solubilized in one of these abovementioned solvents, is added. The reaction is preferably carried out under a stream of inert gas, such as nitrogen or argon.

The compositions which are the subject of the invention are essentially characterized in that they are topical compositions containing, in a vehicle suitable for topical application, at least one of the compounds corresponding to formula (I) above.

The compositions may take the form of a solution, emulsion, suspension, gel or vesicle dispersion, containing at least one compound corresponding to the formula (I) in concentrations of between 0.00001 and 1% by weight with respect to the total weight of the composition, and preferably between 0.001 and 1%.

The compositions can contain vehicles and adjuvants which are acceptable for topical application and well known in the state of the art. It is possible, for example, to prepare solutions using one or more organic solvent(s) which is/are acceptable from the physiological standpoint, chosen, in addition to water, from solvents such as acetone, ethanol, isopropyl alcohol, glycol ethers such as the products sold under the name of "Dowanol", polyglycols such as polyethylene glycols and polypropylene glycols, short-chain organic acid esters such as, preferably, $C_1$–$C_4$ alkyl lactates, fatty acid esters such as, for example, isopropyl myristate, triglycerides of natural or synthetic origin, and mineral waxes and oils.

The compositions according to the invention can also contain ionic and/or preferably nonionic surfactants, ionic and/or preferably nonionic polymers, of natural or synthetic origin, especially proteins, cellulose and/or cellulose derivatives, guar gum, carob gum, gum arabic, bioheteropolysaccharides such as xanthan gum, chitin, chitosan or its derivatives, or alternatively bentones and montmorillonities, and the like.

It is possible to add, if necessary, an adjuvant chosen from antioxidants, surfactants, other preservatives, keratolytic or comedolytic agents, perfumes and colourings.

For example, among antioxidants, there may be mentioned t-butylhydroquinone, butylated hydroxyanisole, butylated hydroxytoluene and α-tocopherol and its derivatives.

The galenical forms mainly packaged for topical application take the form of creams, milks, gels, dispersions or microemulsions, vesicles, more or less thickened lotions, impregnated pads, ointments or sticks, or alternatively the form of aerosol formulations in spray or foam form, or alternatively the form of a cake of soap.

The compositions according to the invention are especially suitable for the treatment of various dermatoses such as acne. In this case, they can also contain, in a pharmaceutically acceptable medium, in combination with the compound of formula (I), anti-acne agents such as antibacterial and anti-inflammatory agents and antiseborrhoeic compounds.

The compounds according to the invention, when used for treating hair loss or for stimulating hair regrowth, may be combined with agents which promote regrowth, and more especially pyrimidine derivatives such as 2,4-diamino-6-piperidinopyrimidine 3-oxide, also known as Minoxidil, 7-chloro-3-methyl-1,2,4-benzothiadiazine 1,1-dioxide or Diazoxide, and 5,5-diphenylimidazolidine-2,4-dione or Phenytoin.

A subject of the invention resides in the use of the compounds of the formula (I) for the preparation of such compounds intended for the treatment of dermatoses.

The compositions according to the invention can also be used for the cosmetic treatment of the skin, in particular as comedolytic and keratolytic agents.

These compositions can contain, in a cosmetically acceptable medium, adjuvants customarily used in cosmetics in compositions intended for the care and cosmetic treatment of the skin.

The method of cosmetic treatment consists in applying such a composition on the skin for a period of 2 to 6 months.

The antibacterial activity of the compounds according to the invention was studied by the dilution method, for the purpose of determining the minimal inhibitory concentration (M.I.C.) according to the method described and used by G. A. Denys et al., Antimicrobial Agents and rhemotherapy (1983) 23, 335–337 and J. J. Leyden et al., J. Am. Acad. Dermatol. (1983) 8 (1) 41–5, using the strain ATCC 6919 as the strain of *Propionibacterium acnes*.

The minimal inhibitory concentrations (M.I.C.) expressed in μg/ml (DMSO) of the quaternary ammonium retinoates according to the invention are shown in Table I.

TABLE I

| | | M.I.C. TESTS | | | | | |
|---|---|---|---|---|---|---|---|
| No | COMPOUND NAME | M.I.C. (μg/ml) ATCC 6919 | $R_1$ | $R_2$ | $R_3$ | $R_4$ | COUNTER-ANION |
| 1* | N—Hexadecyl-N,N,N—trimethylammonium oleate | 12 | —$CH_3$ | —$CH_3$ | —$CH_3$ | n-$C_{16}H_{33}$ | Oleate |
| 2 | N—Hexadecyl-N,N,N—trimethylammonium all-trans-retinoate | 2.2 | —$CH_3$ | —$CH_3$ | —$CH_3$ | n-$C_{16}H_{33}$ | All-trans-Retinoate |
| 3 | N—Hexadecyl-N,N,N—trimethylammonium 13-cis-retinoate | 3 | —$CH_3$ | —$CH_3$ | —$CH_3$ | n-$C_{16}H_{33}$ | 13-cis-Retinoate |
| 4 | N—Benzyl-N,N—dimethyl-N—hexadecylammonium all-trans-retinoate | 0.6 | —$CH_3$ | —$CH_3$ | —$CH_2$—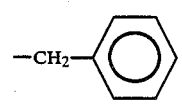 | n-$C_{16}H_{33}$ | All-trans-Retinoate |

TABLE I-continued

| | | M.I.C. TESTS | | | | |
|---|---|---|---|---|---|---|
| No | COMPOUND NAME | M.I.C. (μg/ml) ATCC 6919 | $R_1$ | $R_2$ | $R_3$ | $R_4$ | COUNTER-ANION |
| 5 | N—Benzyl-N,N—dimethyl-N—hexadecylammonium 13-cis-retinoate | 1.1 | —CH$_3$ | —CH$_3$ | —CH$_2$—C$_6$H$_5$ | n-C$_{16}$H$_{33}$ | 13-cis-Retinoate |
| 6 | N—Hexadecyl-N,N—dimethyl-N—(β-hydroxyethyl)ammonium all-trans-retinoate | 1.4 | —CH$_3$ | —CH$_3$ | —C$_2$H$_4$CH | n-C$_{16}$H$_{33}$ | All-trans-Retinoate |
| 7 | Dodecyl-N—ethyl-N,N—dimethylammonium all-trans-retinoate | 0.8 | —CH$_3$ | —CH$_3$ | —C$_2$H$_5$ | n-C$_{12}$H$_{25}$ | All-trans-Retinoate |
| 8 | N—Methyl-N—dodecylmorpholinium all-trans-retinoate | 3.5 | morpholinium ring | | —CH$_3$ | n-C$_{12}$H$_{25}$ | All-trans-Retinoate |
| 9 | N—Dodecyl-N,N—trimethyl-ammonium all-trans-retinoate | 3 | —CH$_3$ | —CH$_3$ | —CH$_3$ | n-C$_{12}$H$_{25}$ | All-trans-retinoate |

*Controls

From a study of this table, it is apparent that the quaternary ammonium retinoates (all-trans and 13-cis) according to the invention are markedly more active with respect to the strain or *Propionibacterium acnes* than hexadecyltrimethylammonium oleate, chosen as reference substance.

The examples below are designed to illustrate, on the one hand, the processes for preparing the compounds according to the invention, and on the other hand pharmaceutical and cosmetic compositions employing these compounds.

PREPARATION EXAMPLE 1

Preparation of N-hexadecyl-N,N,N-trimethyl-ammonium all-trans-retinoate: compound No. 2

Table I 5 g (16.6 mmol) of all-trans-retinoic acid, which was previously dissolved in 50 ml of anhydrous tetrahydrofuran, were added to a solution of 5.25 g (8.3 mmol) of freshly purified and dried hexadecyltrimethylammonium carbonate dissolved in 50 ml of anhydrous methanol; the mixture was stirred for 2 hours at 30° C., away from the light and under an inert atmosphere, then the solvents were evaporated off under high vacuum and the residue obtained was taken up in heptane; the solution was filtered and the solvent was evaporated off under high vacuum. 9.7 g (quantitative yield) of N-hexadecyl-N,N,N-trimethylammonium all-trans-retinoate were obtained in the form of a maroon paste.

Elemental anlysis: $C_{39}H_{69}NO_2, 1H_2O$; M=602.

| | C | H | N |
|---|---|---|---|
| Calculated %: | 77.82 | 11.89 | 2.32 |
| Found %: | 77.44 | 12.04 | 2.00 |

$^{13}$C and $^1$H N.M.R. (CDCl$_3$, internal standard T.M.S.)

The $^1$H and $^{13}$C N.M.R. spectra confirmed the expected structure; the $^{13}$C N.M.R. spectrum in particular indicates a shift towards the low fields (+7.6 ppm) for C-14 which is due to the formation of the quaternary ammonium retinoate; lastly, the $^1$H N.M.R. spectrum specifies that the stereochemistry of the retinoic chain was all-trans because of the H-12 chemical shift at 6.3 ppm. U.V. spectrum (ethanol) γmax=336 nm εmol=41579.

PREPARATION EXAMPLE 2

Preparation of N-hexadecyl-N,N,N-trimethylammonium 13-cis-retinoate; compound No. 3

Table I 5 g (16.6 mmol) of 13-cis-retinoic acid, which was previously dissolved in 50 ml of anhydrous tetrahydrofuran, were added to a solution of 5.25 g (8.3 mmol) of freshly purified and dried hexadecyltrimethylammonium carbonate dissolved in 50 ml of anhydrous methanol; the mixture was stirred for 2 hours at 30° C., away from the light and under an inert atmosphere, then the solvents were evaporated off under high vacuum and the residue obtained was taken up in heptane; the solution was filtered and the solvent was evaporated off under high vacuum. 9.7 g (quantitative yield) of N-hexadecyl-N,N,N-trimethylammonium 13-cis-retinoate were obtained in the form of a brown paste.

Elemental analysis: $C_{39}H_{69}NO_2.1.5H_2O$; M=611.

| | C | H | N |
|---|---|---|---|
| Calculated %: | 76.67 | 11.54 | 2.29 |
| Found %: | 77.06 | 11.68 | 2.21 |

$^1$H and $^{13}$C N.M.R. (CDCl$_3$, internal standard T.M.S.)

The $^1$H N.M.R. spectrum confirms the 13-cis structure of the retinoate chain with the H$_{12}$ chemical shift at 7.9 ppm: the $^{13}$C N.M.R. spectrum indicates a shift towards the low fields (⇌9 ppm) for C$_{14}$ which is due to the formation of the retinoate counteranion. U.V. spectrum (ethanol) γmax=339 nm εmol=30600.

PREPARATION EXAMPLE 3

Preparation of N-benzyl-N,N-dimethyl-N-hexadecylammonium all-trans-retinoate; compound No. 4

Table I 5 g (16.6 mmol) of all-trans-retinoic acid, which was previously dissolved in 50 ml of anhydrous tetrahydrofuran, were added to a solution of 6.5 g (8.3 mmol) of freshly purified and dried benzyldiethylhexadecylammonium carbonate dissolved in 50 ml of anhydrous methanol; the mixture was stirred for 2 hours at 30° C. away from the light and under an inert atmosphere, then the solvents were evaporated off under high vacuum and the residue obtained was taken up in heptane; the solution was filtered and the solvent was evaporated off under high vacuum. 10.9 g (quantitative yield) of N-benzyl-N,N-dimethyl-N-hexadecylammonium all-trans-retinoate were obtained in the form of a brown paste.

Elemental analysis: $C_{45}H_{73}NO_2.H_2O$; M=678.

|  | C | H | N |
|---|---|---|---|
| Calculated %: | 79.77 | 11.07 | 2.06 |
| Found %: | 79.79 | 11.11 | 2.1 |

$^{13}C$ N.M.R. (CDCl$_3$, internal standard T.M.S.)

7.3 ppm shift towards the low fields for the $C_{14}$, which indicates the formation of the quaternary ammonium retinoate counteranion; $C_{20}$ peak at 13.68 ppm, which confirms the all-trans stereochemistry of the retinoic chain; peak of the ammonium methyl groups at 49.64 ppm. U.V. spectrum (ethanol) γmax=335 εmol=30378.

PREPARATION EXAMPLE 4

Preparation of the N-benzyl-N,N-dimethyl-N-hexadecylammonium 13-cis-retinoate: compound No. 5

Table I 5 g (16.6 mmol) of 13-cis retinoic acid which was previously dissolved in 50 ml of anhydrous tetrahydrofuran, were added to a solution of 6.5 g (8.3 mmol) of freshly purified and dried benzyldimethylhexadecylammonium carbonate dissolved in 50 ml of anhydrous methanol; the mixture was stirred for 2 hours at 30° C. away from the light and in an inert atmosphere, then the solvents were evaporated off under high vacuum and the residue obtained was taken up in heptane; the solution was filtered and the solvent was evaporated off under high vacuum. 10.9 g (quantitative yield) of N-benzyl-N,N-dimethyl-N-hexadecylammonium 13-cis-retinoate were obtained in the form of a maroon paste.

Elemental analysis: $C_{45}H_{73}NO_2.H_2O$; M=678.

|  | C | H | N |
|---|---|---|---|
| Calculated %: | 79.77 | 11.07 | 2.06 |
| Found %: | 79.38 | 11.14 | 1.98 |

$^{13}C$ N.M.R. (CDCl$_3$, internal standard T.M.S.)

9 ppm shift towards the low fields for the $C_{-14}$ which indicates the formation of the quaternary ammonium retinoate counteramion; $C_{-20}$ peak at 20.41 ppm which confirms the 13-cis stereochemistry of the retinoic chain; peak of the ammonium methyl groups at 49.56 ppm. U.V. spectrum (ethanol) γmax=336 εmol=37772.

PREPARATION EXAMPLE 5

Preparation of N,N-dimethyl-N-hexadecyl-N-(β-hydroxyethyl)ammonium all-trans-retinoate: compound No. 6

Table I 5 g (16.6 mmol) of all-trans retinoic acid, which were previously dissolved in 50 ml of anhydrous tetrahydrofuran, were added to a solution of 5.75 g (8.3 mmol) of freshly purified and dried dimethylhexadecyl-(β-hydroxyethyl)ammonium carbonate dissolved in 50 ml of anhydrous methanol; the mixture was stirred for 4 hours at 30° C. away from the light and in an inert atmosphere, then the solvents were evaporated off under high vacuum and the residue obtained was taken up in ethyl acetate; the solution was filtered and the solvent was evaporated off under high vacuum. 10 g (quantitative yield) of N,N-dimethyl-N-(β-hydroxyethyl)-N-hexadecylammonium all-trans-retinoate were obtained in the form of a brown paste.

Elemental analysis: $C_{40}H_{71}NO_3.H_2O$; M=632.

|  | C | H | N |
|---|---|---|---|
| Calculated %: | 75.9 | 11.55 | 2.21 |
| Found %: | 75.54 | 11.53 | 1.92 |

$^1H$ N.M.R. (CDCl$_3$, internal standard T.M.S.)

7.8 ppm shift towards the low fields of the $C_{-14}$, which indicates the formation of the quaternary ammonium retinoate counteranion; $C_{-20}$ peak at 13.67 ppm, which confirms the all-trans stereochemistry of the retinoic chain. U.V. spectrum (ethanol) γmax=328 εmol=31051.

PREPARATION EXAMPLE 6

Preparation of N-dodecyl-N-ethyl-N,N-dimethylammonium all-trans-retinoate: compound No. 7

Table I

This compound was prepared according to the operating conditions described in the preceding examples.

Elemental analysis: $C_{36}H_{63}NO_2.2H_2O$; M=577.9.

|  | C | H | N |
|---|---|---|---|
| Calculated %: | 74.8 | 11.68 | 2.42 |
| Found %: | 75.1 | 11.34 | 2.08 |

$^{13}C$ N.M.R. (CDCl$_3$, internal standard T.M.S.)

7.7 ppm shift towards the low fields of the $C_{-14}$, which indicates the formation of the quaternary ammonium retinoate counteranion; $C_{-20}$ peak at 13.66 ppm which confirms the all-trans stereochemistry of the retinoic chain; peak of the methyl groups carried by the ammonium at 50.46 ppm. U.V. spectrum (ethanol) γmax=336 εmol=38625.

PREPARATION EXAMPLE 7

Preparation of N-dodecyl-N-methylmorpholinium all-trans-retinoate: compound No. 8

Table I

This compound was prepared according to the operating conditions described in the preceding examples.

Elemental analysis: $C_{37}H_{63}NO_3 \cdot 0.5H_2O$; M=578.9.

|  | C | H | N |
|---|---|---|---|
| Calculated %: | 76.76 | 11.14 | 2.42 |
| Found %: | 76.62 | 10.95 | 2.20 |

[13]C N.M.R. (CDCl$_3$, internal standard T.M.S.)

7.9 ppm shift towards the low fields of the C-$_{14}$, which indicates the formation of the quaternary ammonium retinoate counteranion; C-$_{20}$ peak at 13.78 ppm; peak of the methyl group carried by the ammonium at 46.94 ppm. U.V. spectrum (ethanol) $\gamma$max=336 $\epsilon$mol=38416.

PREPARATION EXAMPLE 8

Preparation of the N-dodecyl-N,N,N-trimethylammonium all-trans-retinoate: compound No. 9

Table I

This compound was prepared according to the operating conditions described in the preceding examples.
Elemental analysis: $C_{35}H_{61}NO_2 \cdot H_2O$; M=545.9.

|  | C | H | N |
|---|---|---|---|
| Calculated %: | 77.1 | 11.63 | 2.56 |
| Found %: | 77.11 | 11.49 | 2.28 |

[13]C N.M.R. (CDCl$_3$, internal standard T.M.S.)

7.5 ppm shift towards the low fields of the C-$_{14}$, which indicates the formation of the quaternary ammonium retinoate counteranion; C-$_{20}$ peak at 13.64 ppm; peak of the methyl groups carried by the ammonium at 52.97 ppm.

EXAMPLES OF COMPOSITIONS

The following anti-acne compositions were prepared:

EXAMPLE 1
| Hydroxypropylcellulose | 1.5 g |
|---|---|
| Butylated hydroxytoluene | 0.05 g |
| Hexadecyltrimethylammonium all-trans-retinoate | 0.03 g |
| Anhydrous isopropanol qs | 100 g |

This composition is presented in the form of a gel.

EXAMPLE 2
| Hydroxypropylcellulose | 1.5 g |
|---|---|
| Butylated hydroxytoluene | 0.05 g |
| Hexadecyltrimethylammonium 13-cis-retinoate | 0.02 g |
| Anhydrous ethanol qs | 100 g |

This composition is presented in the form of a gel.

EXAMPLE 3
| Hydroxypropylcellulose | 1.5 g |
|---|---|
| Butylated hydroxytoluene | 0.04 g |
| $C_8$-$C_{12}$ fatty acid triglycerides | 10.00 g |
| Dimethylbenzylhexadecylammonium all-trans-retinoate | 0.025 g |
| Anhydrous isopropanol qs | 100 g |

This composition is presented in the form of a gel.

EXAMPLE 4
| Hydroxypropylcellulose | 1.5 g |
|---|---|
| Butylated hydroxytoluene | 0.05 g |
| Ethyl lactate | 10.00 g |
| Dimethylbenzylhexadecylammonium 13-cis-retinoate | 0.03 g |
| Anhydrous isopropanol qs | 100 g |

This composition is presented in the form of a gel.

EXAMPLE 5
| Hexadecyltrimethylammonium all-trans-retinoate | 0.1 g |
|---|---|
| Butylated hydroxytoluene | 0.05 g |
| Anhydrous isopropanol qs | 100 g |

This composition is presented in the form of a lotion.

EXAMPLE 6
| Hexadecyltrimethylammonium 13-cis-retinoate | 0.15 g |
|---|---|
| Butylated hydroxytoluene | 0.05 g |
| Anhydrous ethanol qs | 100 g |

This composition is presented in the form of a lotion.

EXAMPLE 7
| $C_8$-$C_{12}$ fatty acid triglycerides | 15.00 g |
|---|---|
| Dodecyltrimethylammonium all-trans-retinoate | 0.20 g |
| Butylated hydroxytoluene | 0.05 g |
| Anhydrous isopropanol qs | 100 g |

This composition is presented in the form of a lotion.

EXAMPLE 8
| White vaseline | 50.00 g |
|---|---|
| Vaseline oil | 15.00 g |
| Refined paraffin | 34.93 g |
| Hexadecyltrimethylammonium all-trans-retinoate | 0.02 g |
| Butylated hydroxytoluene | 0.05 g |

This composition is presented in the form of a stick.

Indications for use: the preceding formulations may be applied every evening on the areas to be treated for a period of 2 to 6 months.
A regression of the acne is observed after a few weeks of treatment.

EXAMPLE 9
The following wart-removing lotion is prepared:

| Hexadecyltrimethylammonium all-trans-retinoate | 0.1 g |
|---|---|
| Butylated hydroxytoluene | 0.05 g |
| Anhydrous isopropanol qs | 100 g |

This solution is applied once a day on the warts for a period of 2 to 4 weeks.

EXAMPLE 10
The following anti-dandruff lotion is prepared:

| Benzyltrimethylammonium all-trans-retinoate | 0.001 g |
|---|---|
| Butylated hydroxytoluene | 0.05 g |
| Anhydrous isopropanol qs | 100 g |

This lotion is applied on the scalp once a day for 15 days and then twice a week for 1 month.

EXAMPLE 11
The following lotion is prepared, which is active against seborrhoeic dermatitis:

| Hexadecyltrimethylammonium 13-cis-retinoate | 0.005 g |
|---|---|
| Butylated hydroxytoluene | 0.05 g |
| Anhydrous isopropanol qs | 100 g |

This lotion is applied on the areas to be treated once a day for a period of 3 to 4 weeks.

EXAMPLE 12
The following lotion is prepared, which is active against psoriasis:

| Hexadecyltrimethylammonium all-trans-retinoate | 0.001 g |
|---|---|
| Butylated hydroxytoluene | 0.05 g |
| Anhydrous isopropanol qs | 100 g |

This composition is applied on the areas to be treated once or twice a day for 15 days.

We claim:
1. Quaternary ammonium retinoate of formula

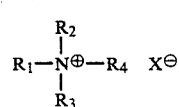

in which:
$X^-$ denotes:
either an all-trans-retinoate of formula:

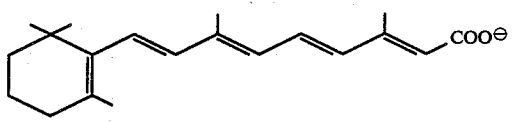

or a 13-cis-retinoate of formula:

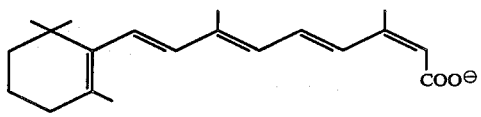

(i) $R_1$, $R_2$ and $R_3$, which may be identical or different, denote a saturated $C_1$–$C_4$ linear alkyl group capable of bearing one or more hydroxyl group(s) at the end of the chain or in the chain;

$R_4$ denotes a $C_{12}$–$C_{18}$ linear alkenyl or alkyl group;

(ii) $R_3$ denotes a group;

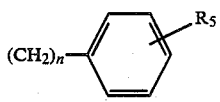

in which n equals 0 or 1, $R_5$ denotes a hydrogen atom, a hydroxyl, a halogen atom, a $C_1$–$C_{18}$ hydroxyl alkyl or alkyl group;

$R^1$, $R^2$ and $R^4$ having the same meanings as those under (i);

$R^3$ and $R^4$ having the same meanings as those under (i) and (ii).

2. Compounds according to claim 1, wherein $R_3$ denotes a benzyl group and $R_1$, $R_2$ and $R_4$ have the meanings stated in (i) and (ii).

3. Compounds according to claim 1 selected from the group consisting of:
N-hexadecyl-N,N,N-trimethylammonium all-trans-retinoate, N-hexadecyl-N,N,N-trimethylammonium 13-cis-retinoate, N-benzyl-N,N,-dimethyl-N-hexadecylammonium all-trans-retinoate, N-benzyl-N,N-dimethyl-N-hexadecylammonium 13-cis-retinoate, N-hexadecyl-N,N-dimethyl-N-(β-hydroxyethyl)ammonium all-trans-retinoate, N-dodecyl-N-ethyl-N,N-dimethylammonium all-trans-retinoate, N-methyl-N-dodecylmorpholinium all-trans-retinoate and N-dodecyl-N,N,N-trimethylammonium all-trans-retinoate.

4. A composition, containing at least one compound as defined in claim 1 in a vehicle suitable for topical application.

5. A composition according to claim 4, taking the form of a solution, emulsion, suspension, gel or vesicle dispersion containing at least one compound of the formula (I) in concentrations of between 0.00001 and 1% by weight with respect to the total weight of the composition.

6. A composition according to claim 4, taking the form of a cream, milk gel, dispersion or microemulsion, more or less thickened lotion, impregnated pad, ointment or stick, or the form of a spray or foam, or alternatively the form of a cake of soap.

7. Method for therapeutically treating skin infections or non infectious dermatoses wherein a composition as defined in claim 4 is used.

8. Method of treatment of acne by using a composition as defined in claim 4.

* * * * *